(12) United States Patent
Babu et al.

(10) Patent No.: US 8,354,528 B2
(45) Date of Patent: Jan. 15, 2013

(54) PROCESS FOR MAKING THIENOPYRIMIDINE COMPOUNDS

(75) Inventors: Srinivasan Babu, South San Francisco, CA (US); Zhigang Cheng, South San Francisco, CA (US); Mark E. Reynolds, South San Francisco, CA (US); Scott J. Savage, South San Francisco, CA (US); Qingping Tian, South San Francisco, CA (US); Herbert Yajima, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 175 days.

(21) Appl. No.: 12/739,434

(22) PCT Filed: Oct. 24, 2008

(86) PCT No.: PCT/US2008/081204
§ 371 (c)(1),
(2), (4) Date: Jul. 29, 2010

(87) PCT Pub. No.: WO2009/055730
PCT Pub. Date: Apr. 30, 2009

(65) Prior Publication Data
US 2010/0292468 A1    Nov. 18, 2010

Related U.S. Application Data

(60) Provisional application No. 60/982,562, filed on Oct. 25, 2007.

(51) Int. Cl.
*C07D 413/14* (2006.01)
(52) U.S. Cl. ...................................................... 544/121
(58) Field of Classification Search .................... 544/121
See application file for complete search history.

(56) References Cited

U.S. PATENT DOCUMENTS

| | | | |
|---|---|---|---|
| 3,475,429 A | 10/1969 | Woitun et al. | |
| 3,661,908 A | 5/1972 | Woitun et al. | |
| 3,763,156 A | 10/1973 | Woitun et al. | |
| 3,883,651 A | 5/1975 | Woitun et al. | |
| 3,888,851 A | 6/1975 | Narr et al. | |
| 4,007,187 A | 2/1977 | Fauran et al. | |
| 4,146,716 A | 3/1979 | Cox et al. | |
| 4,196,207 A | 4/1980 | Webber et al. | |
| 5,075,305 A | 12/1991 | Hobbs et al. | |
| 6,048,863 A | 4/2000 | Furuya et al. | |
| 6,187,777 B1 | 2/2001 | Norman et al. | |
| 6,399,779 B1 | 6/2002 | Marcuccio et al. | |
| 6,492,383 B1 | 12/2002 | Munchhof et al. | |
| 6,555,539 B2 | 4/2003 | Reich et al. | |
| 6,608,056 B1 | 8/2003 | Hayakawa et al. | |
| 7,217,677 B2 | 5/2007 | Itahashi et al. | |
| 7,595,324 B2 * | 9/2009 | Girardet et al. | 514/260.1 |
| 7,750,002 B2 | 7/2010 | Shuttleworth et al. | |
| 7,776,856 B2 | 8/2010 | Shuttleworth et al. | |
| 7,781,433 B2 | 8/2010 | Chuckowree et al. | |
| 2004/0192728 A1 | 9/2004 | Codd et al. | |
| 2006/0094881 A1 | 5/2006 | Ewanicki et al. | |
| 2006/0229306 A1 | 10/2006 | Terricabras Belart et al. | |

(Continued)

FOREIGN PATENT DOCUMENTS

| | | |
|---|---|---|
| WO | 2006/048745 A1 | 5/2006 |
| WO | 2008/152394 A1 | 12/2008 |
| WO | 2009/053715 A1 | 4/2009 |
| WO | 2010/110782 A1 | 9/2010 |

OTHER PUBLICATIONS

Tor et al., Tetrahedron 63 (2007) 3608-3614.* Bourguinon et al., "Synthesis of 2- and 4-substituted thieno [2,3-d]pyrimidines II" *Bulletin de la Societe Chimique de France* 11-12:2483-2487 (1974).
Bourguinon et al., "Synthesis of thieno [2,3-d]pyrimidines substituted at 2 and 4" *Bulletin de la Societe Chimique de France* 3-4(pt 2):815-819 (1975).

(Continued)

*Primary Examiner* — Rebecca Anderson
(74) *Attorney, Agent, or Firm* — Alex Andrus; Genentech, Inc.

(57) ABSTRACT

The invention provides processes of preparing, separating, and purifying PI3K inhibitor, Formula (I) and (II) compounds, and novel intermediates for preparing Formula (I) and (II) compounds.

(I)

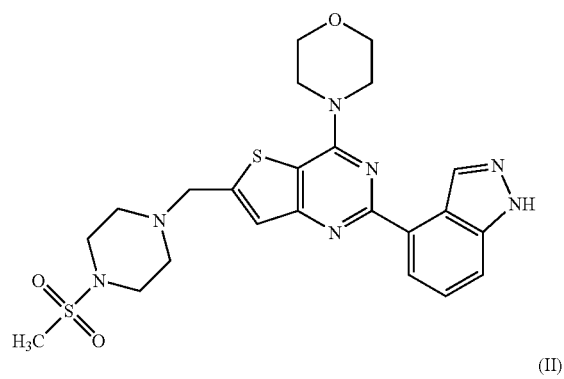

(II)

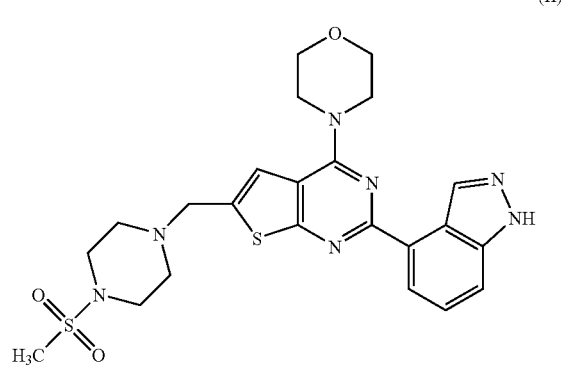

5 Claims, No Drawings

U.S. PATENT DOCUMENTS

| | | |
|---|---|---|
| 2007/0244131 A1 | 10/2007 | Lim et al. |
| 2007/0249587 A1 | 10/2007 | Yonetoku et al. |
| 2008/0039459 A1 | 2/2008 | Folkes et al. |
| 2008/0076758 A1 | 3/2008 | Folkes et al. |
| 2008/0207609 A1 | 8/2008 | Shuttleworth et al. |
| 2008/0242665 A1 | 10/2008 | Bayliss et al. |
| 2008/0269210 A1 | 10/2008 | Castanedo et al. |
| 2008/0306060 A1 | 12/2008 | Alexander et al. |
| 2009/0209559 A1 | 8/2009 | Chuckowree et al. |
| 2009/0318411 A1 | 12/2009 | Castanedo et al. |
| 2010/0016306 A1 | 1/2010 | Baker et al. |

OTHER PUBLICATIONS

Briel et al., "Selective Nucleophilic Replacement of the Benzylsulfanyl Group in 2,4-Disulfanyl-substituted Thieno[2,3-d]pyrimidin-6-carboxylic Acid Derivatives by Secondary Amines" *Journal Heterocyclic Chem.* 42(5):841-846 (Jul.-Aug. 2005).

Sutherlin at al., "Discovery of (Thienopyrimidin-2-yl)aminopyrimidines as Potent, Selective, and Orally Available Pan-PI3-Kinase and Dual Pan-PI3-Kinase/mTOR Inhibitors for the Treatment of Cancer" *Journal of Medicinal Chemistry* 53(3):1086-1097 (2010).

\* cited by examiner

PROCESS FOR MAKING THIENOPYRIMIDINE COMPOUNDS

CROSS REFERENCE TO RELATED APPLICATIONS

This non-provisional application filed under 37 CFR §1.53 (b), claims the benefit under 35 USC §119(e) of U.S. Provisional Application Ser. No. 60/982,562 filed on 25 Oct. 2007, which is incorporated by reference in entirety.

FIELD OF THE INVENTION

The invention relates generally to processes for making and purifying thienopyrimidine compounds with anti-cancer activity and more specifically to compounds which inhibit PI3 kinase activity.

BACKGROUND OF THE INVENTION

Phosphatidylinositol (hereinafter abbreviated as "PI") is one of a number of phospholipids found in cell membranes. In recent years it has become clear that PI plays an important role in intracellular signal transduction. Cell signaling via 3'-phosphorylated phosphoinositides has been implicated in a variety of cellular processes, e.g., malignant transformation, growth factor signaling, inflammation, and immunity (Rameh et al (1999) J. Biol Chem, 274:8347-8350). The enzyme responsible for generating these phosphorylated signaling products, phosphatidylinositol 3-kinase (also referred to as PI 3-kinase or PI3K), was originally identified as an activity associated with viral oncoproteins and growth factor receptor tyrosine kinases that phosphorylate phosphatidylinositol (PI) and its phosphorylated derivatives at the 3'-hydroxyl of the inositol ring (Panayotou et al (1992) Trends Cell Biol 2:358-60).

Phosphoinositide 3-kinases (PI3K) are lipid kinases that phosphorylate lipids at the 3-hydroxyl residue of an inositol ring (Whitman et al (1988) Nature, 332:664). The 3-phosphorylated phospholipids (PIP3s) generated by PI3-kinases act as second messengers recruiting kinases with lipid binding domains (including plekstrin homology (PH) regions), such as Akt and phosphoinositide-dependent kinase-1 (PDK1). Binding of Akt to membrane PIP3s causes the translocation of Akt to the plasma membrane, bringing Akt into contact with PDK1, which is responsible for activating Akt. The tumor-suppressor phosphatase, PTEN, dephosphorylates PIP3 and therefore acts as a negative regulator of Akt activation. The PI3-kinases Akt and PDK1 are important in the regulation of many cellular processes including cell cycle regulation, proliferation, survival, apoptosis and motility and are significant components of the molecular mechanisms of diseases such as cancer, diabetes and immune inflammation (Vivanco et al (2002) Nature Rev. Cancer 2:489; Phillips et al (1998) Cancer 83:41).

The main PI3-kinase isoform in cancer is the Class I PI3-kinase, p110α (alpha) (U.S. Pat. No. 5,824,492; U.S. Pat. No. 5,846,824; U.S. Pat. No. 6,274,327). Other isoforms are implicated in cardiovascular and immune-inflammatory disease (Workman P (2004) Biochem Soc Trans 32:393-396; Patel et al (2004) Proceedings of the American Association of Cancer Research (Abstract LB-247) 95th Annual Meeting, March 27-31, Orlando, Fla., USA; Ahmadi K and Waterfield Md. (2004) Encyclopedia of Biological Chemistry (Lennarz W J, Lane M D eds) Elsevier/Academic Press).

The PI3 kinase/Akt/PTEN pathway is an attractive target for cancer drug development since such agents would be expected to inhibit proliferation, reverse the repression of apoptosis and surmount resistance to cytotoxic agents in cancer cells. PI3 kinase inhibitors have been reported (Yaguchi et al (2006) Jour. of the Nat. Cancer Inst. 98(8):545-556; U.S. Pat. No. 7,173,029; U.S. Pat. No. 7,037,915; U.S. Pat. No. 6,608,056; U.S. Pat. No. 6,608,053; U.S. Pat. No. 6,838,457; U.S. Pat. No. 6,770,641; U.S. Pat. No. 6,653,320; U.S. Pat. No. 6,403,588; U.S. Pat. No. 6,703,414; WO 97/15658; WO 2006/046031; WO 2006/046035; WO 2006/046040; WO 2007/042806; WO 2007/042810; WO 2004/017950; US 2004/092561; WO 2004/007491; WO 2004/006916; WO 2003/037886; US 2003/149074; WO 2003/035618; WO 2003/034997; US 2003/158212; EP 1417976; US 2004/053946; JP 2001247477; JP 08175990; JP 08176070).

Thienopyrimidine compounds, including Formula I and II compounds, have p110 alpha binding, PI3 kinase inhibitory activity and inhibit the growth of cancer cells (WO 2006/046031; US 2008/0039459; US 2008/0076768; US 2008/0076758; WO 2008/070740; WO 2008/073785).

Formula I compound, GDC-0941 (Genentech Inc.), is a selective, orally bioavailable inhibitor of PI3K with promising pharmacokinetic and pharmaceutical properties (Folkes et al (2008) Jour. Med. Chem. 51:5522-5532; Belvin et al, American Association for Cancer Research Annual Meeting 2008, 99th: Apr. 15, Abstract 4004; Folkes et al, American Association for Cancer Research Annual Meeting 2008, 99th: Apr. 14, Abstract LB-146; Friedman et al, American Association for Cancer Research Annual Meeting 2008, 99th: Apr. 14, Abstract LB-110).

Therapeutic combinations of Formula I and II compounds, and certain chemotherapeutic agents are described in "COMBINATIONS OF PHOSPHOINOSITIDE 3-KINASE INHIBITOR COMPOUNDS AND CHEMOTHERAPEUTIC AGENTS, AND METHODS OF USE" Belvin et al, filing date 10 Sep. 2008; U.S. Ser. No. 12/208,227.

SUMMARY OF THE INVENTION

An aspect of the invention includes processes of preparing, separating, and purifying compounds of Formulas I and II.

Formula I compound is named as 4-(2-(1H-indazol-4-yl)-6-((4-(methylsulfonyl)piperazin-1-yl)methyl)thieno[3,2-d]pyrimidin-4-yl)morpholine and has the structure:

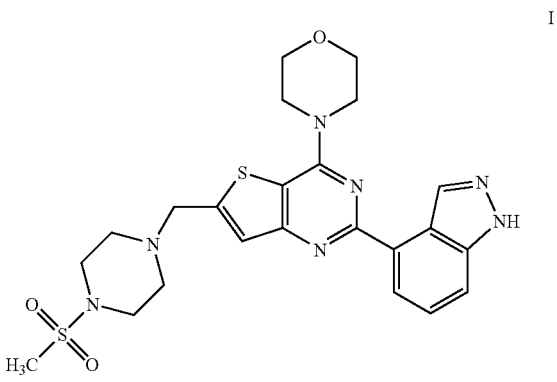 [SMILES: CS(=O)(=O)N1CCN(Cc2cc3nc(-c4cccc5[nH]ncc45)nc(N4CCOCC4)c3s2)CC1]

Formula II compound is named as 4-(2-(1H-indazol-4-yl)-6-((4-(methylsulfonyl)piperazin-1-yl)methy)thieno[2,3-d]pyrimidin-4-yl)morpholine and has the structure:

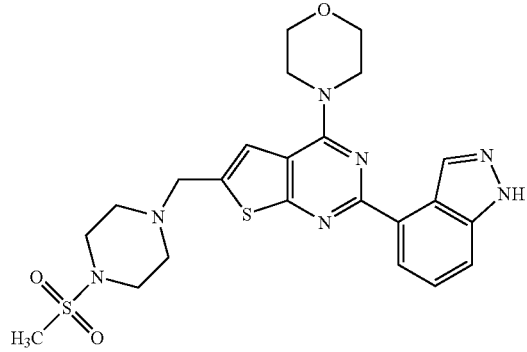

II

Formula I and II compounds include all stereoisomers, geometric isomers, tautomers, metabolites, and pharmaceutically acceptable salts thereof. Formula I and II compounds are potent inhibitors of PI3K with drug-like physicochemical and pharmacokinetic properties. Formula I and II compounds exhibit selectivity for class Ia PI3Ks over class Ib, in particular for the P110 alpha subtype (US 2008/0039459; US 2008/0076768; US 2008/0076758).

Another aspect of the invention includes novel intermediates useful for preparing Formulas I and II compounds including 4-chloro-2-(tetrahydro-2H-pyran-2-yl)-2H-indazole 13 and 2-(tetrahydro-2H-pyran-2-yl)-4-(4,4,5,5-tetramethyl-1,3,2-dioxaborolan-2-yl)-2H-indazole 10

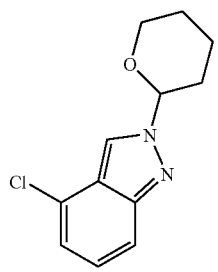

13

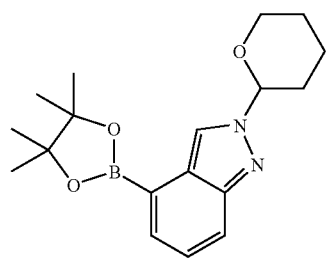

10

4-(6-((4-(methylsulfonyl)piperazin-1-yl)methyl)-2-(2-(tetrahydro-2H-pyran-2-yl)-2H-indazol-4-yl)thieno[3,2-d]pyrimidin-4-yl)morpholine 14, and THP regioisomer 4-(6-((4-(methylsulfonyl)piperazin-1-yl(methyl)-2-(1-(tetrahydro-2H-pyran-2-yl)-1H-indazol-4-yl)thieno[3,2-d]pyrimidin-4-yl(morpholine 14A

14

14A 4-(6-((4-(methylsulfonyl)piperazin-1-yl)methyl)-2-(2-(tetrahydro-2H-pyran-2-yl)-2H-indazol-4-yl)thieno[2,3-d]pyrimidin-4-yl)morpholine 21, and THP regioisomer 4-(6-((4-(methylsulfonyl)piperazin-1-yl)methyl)-2-(1-(tetrahydro-2H-pyran-2-yl)-1H-indazol-4-yl)thieno[2,3-d]pyrimidin-4-yl)morpholine 21A.

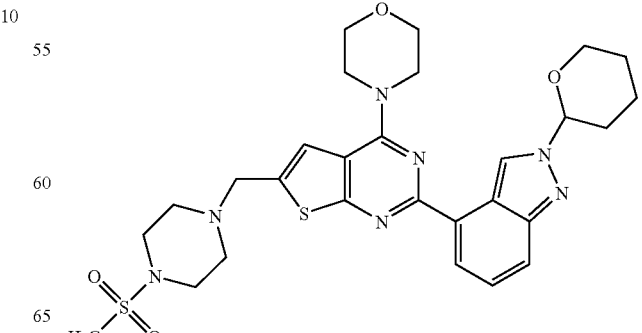

21

21A

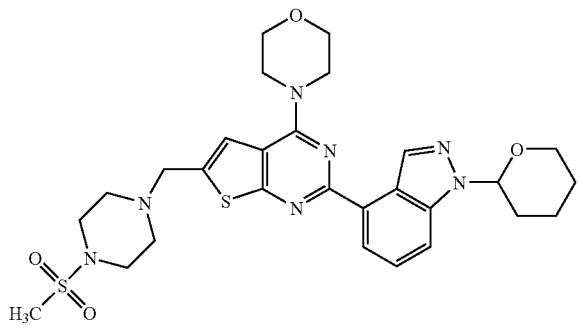

DETAILED DESCRIPTION OF EXEMPLARY EMBODIMENTS

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. The invention is intended to cover all alternatives, modifications, and equivalents which may be included within the scope of the present invention. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

DEFINITIONS

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

Preparation of Formula I and II Compounds

The Formula I and II compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. In addition, the present invention embraces all geometric and positional isomers. In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention embrace both solvated and unsolvated forms.

The compounds of the present invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The present invention also embraces isotopically-labeled compounds of the present invention which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine and iodine, such as $^2H$, $^3H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Certain isotopically-labeled compounds of the present invention (e.g., those labeled with $^3H$ and $^{14}C$) are useful in compound and/or substrate tissue distribution assays. Tritiated ($^3H$) and carbon-14 ($^{14}C$) isotopes are useful for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies to examine substrate receptor occupancy. Isotopically labeled compounds of the present invention can generally be prepared by following procedures analogous to those disclosed in the Examples herein below, by substituting an isotopically labeled reagent for a non-isotopically labeled reagent.

Starting materials and reagents for the preparation of Formula I and II compounds are generally available from commercial sources such as Sigma-Aldrich Chemical (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, N.Y. (1967-1999 ed.), or *Beilsteins Handbuch der organischen Chemie*, 4, Aufl. ed. Springer-Verlag, Berlin, including supplements (also available via the Beilstein online database).

The following Schemes 1-8 illustrate the synthesis of Formula I and II compounds and certain intermediates and reagents.

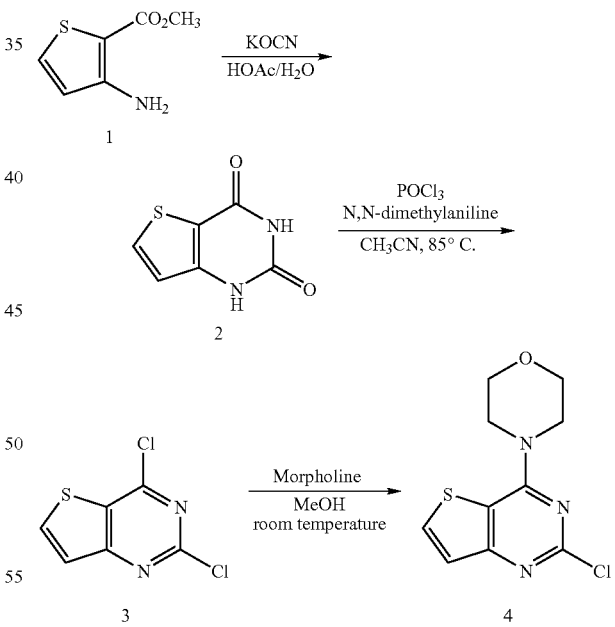

Scheme 1 shows the synthesis of 4-(2-chlorothieno[3,2-d]primidin-4-yl)morpholine 4 starting by cyclization of methyl 3-amino-thiophenecarboxylate 1 and potassium cyanate in acetic acid and water at room temperature to give thieno[3,2-d]pyrimidine-2,4(1H,3H)-dione 2. This is an improvement over cyclization of 1 with urea which requires high temperature and evolution of ammonia gas. Thieno[3,2-d]pyrimidine-2,4(1H,3H)-dione 2 was converted to 2,4-dichlorothieno[3,2-d]pyrimidine 3 with phosphorous oxychloride and a catalytic amount of N,N-dimethylaniline (0.75 equiv.) in acetonitrile. Selective substitution at the 4-position with morpholine gave 4.

Cyclization of methyl 3-aminothiophene-2-carboxylate 1 to thieno[3,2-d]pyrimidine-2,4(1H,3H)-dione 2, and methyl 2-aminothiophene-3-carboxylate 15 to thieno[2,3-d]pyrimidine-2,4(1H,3H)-dione 16 has previously been conducted with urea, requiring high temperature and pressure increase by evolution of ammonia gas (Robba, et al (1975) Bulletin de la Societe Chimique de France (3-4, Pt. 2) 587-91). The present invention replaces urea with potassium cyanate to cyclize 1 to 2 (Example 1), and chlorosulfonyl isocyanate to cyclize 15 to 16 (Scheme 6, Example 12).

Scheme 2

Scheme 2 shows the synthesis of 4-(methylsulfonyl)piperazin-1-ium chloride 8 starting by N-sulfonylation of 1-(tert-butoxycarbonyl)piperazine 6 (BOC-piperazine) with methanesulfonyl chloride to give tert-butyl 4-(methylsulfonyl)piperazine-1-carboxylate 7 which was treated with aqueous hydrogen chloride solution in 1,4-dioxane to give 8.

Scheme 3

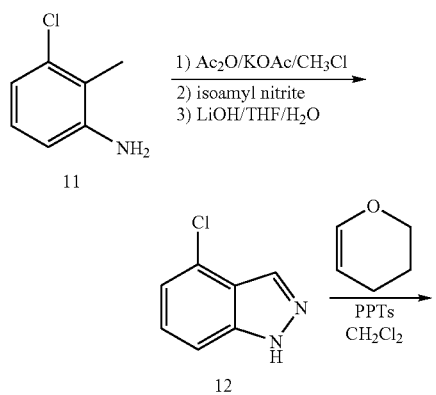

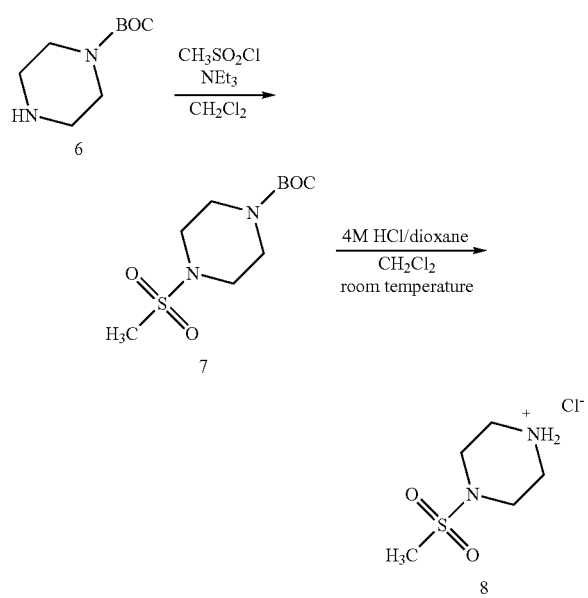

Scheme 3 shows the synthesis of 2-(tetrahydro-2H-pyran-2-yl)-4-(4,4,5,5-tetramethyl-1,3,2-dioxaborolan-2-yl)-2H-indazole 10 starting by cyclization of 3-chloro-2-methylaniline 11 with potassium acetate, acetic anhydride, and isoamyl nitrite to yield 4-chloro-1H-indazole 12. The indazole nitrogen of 4-chloro-1H-indazole 12 was protected as tetrahydropyranyl (THP) with 3,4-dihydro-2H-pyran, and pyridinium p-toluenesulfonate in dichloromethane to yield 4-chloro-2-(tetrahydro-2H-pyran-2-yl)-2H-indazole 13 and a minor amount (about 10%) of the THP regioisomer, 4-chloro-1-(tetrahydro-2H-pyran-2-yl)-1H-indazole. The mixture was reacted with $PdCl_2(PPh_3)_2$, tricyclohexylphosphine, bis(pinacolato)diboron, and potassium acetate in DMSO and heated to 130° C. for 16 hours to give 10, containing a minor amount (about 10%) of the THP regioisomer, 1-(tetrahydro-2H-pyran-2-yl)-4-(4,4,5,5-tetramethyl-1,3,2-dioxaborolan-2-yl)-1H-indazole.

Scheme 4

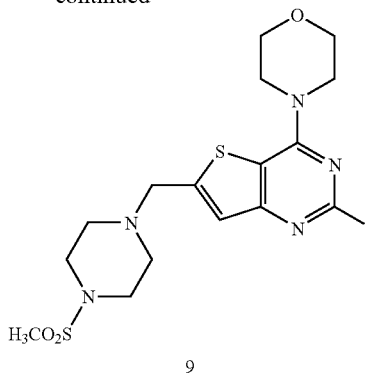

9

Scheme 4 shows the synthesis of 4-(2-chloro-6-((4-(methylsulfonyl)piperazin-1-yl)methyl)thieno[3,2-d]pyrimidin-4-yl)morpholine 9 starting with formylation at the 7-position of 4-(2-chlorothieno[3,2-d]pyrimidin-4-yl)morpholine 4 (1.0 equiv.) in THF with n-BuLi in hexanes to give 2-chloro-4-morpholinothieno[3,2-d]pyrimidine-6-carbaldehyde 5 after acidification. Reductive amination of aldehyde 5 was accomplished with 4-(methylsulfonyl)piperazin-1-ium chloride 8 and sodium acetate (anhydrous powder) in 1,2-dichloroethane. Trimethyl orthoformate was added and stirred for 6 hours, followed by the addition of sodium triacetoxyborohydride to give 9.

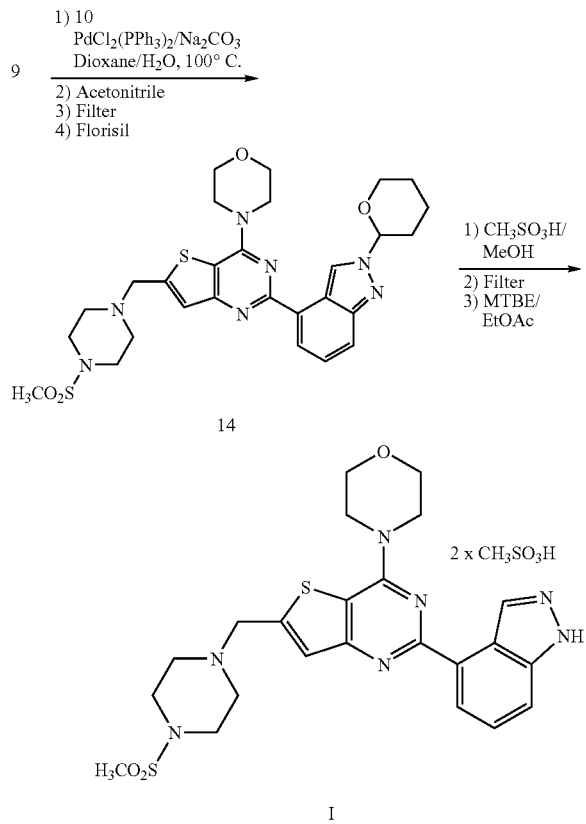

Scheme 5 shows the synthesis of 4-(2-(1H-indazol-4-yl)-6-((4-(methylsulfonyl)piperazin-1-yl)methyl)thieno[3,2-d]pyrimidin-4-yl)morpholine I bis mesylate salt by Suzuki coupling of 4-(2-chloro-6-((4-(methylsulfonyl)piperazin-1-yl)methyl)thieno[3,2-d]pyrimidin-4-yl)morpholine 9 in 1,4-dioxane with 2-(tetrahydro-2H-pyran-2-yl)-4-(4,4,5,5-tetramethyl-1,3,2-dioxaborolan-2-yl)-2H-indazole 10, and bis(triphenylphosphine)palladium (II) chloride in aqueous sodium carbonate. The mixture containing the crude THP protected intermediate 14, along with a minor amount of THP regioisomer 14A, was concentrated, acetonitrile was added, and the slurry was filtered. The resulting cake was dried to afford 14 as a brown-yellow solid with residual Pd content of 2000 ppm. The cake was dissolved in methylene chloride and FLORISIL® (60-100 mesh, Sigma-Aldrich Chemical Company, Inc) as a palladium scavenger was then added. FLORISIL® (U.S. Silica Company) is a magnesium silicate, highly selective adsorbent.

The slurry was stirred at ambient temperature for a minimum of 5 hours, then silica gel adsorbent metal scavenger SILIABOND® Thiol (Silicycle Inc) was added. After a minimum of 12 hour agitation, the mixture was filtered and rinsed with methylene chloride and ethyl acetate. The filtrate and the rinse were concentrated to give 14 as an off-white solid with Pd content of less than 20 ppm.

4-(6-((4-(Methylsulfonyl)piperazin-1-yl)methyl)-2-(2-(tetrahydro-2H-pyran-2-yl)-2H-indazol-4-yl)thieno[3,2-d]pyrimidin-4-yl)morpholine 14 was dissolved in a mixture of methanol and water. Methanesulfonic acid was slowly added and the slurry was stirred at ambient temperature for 1 hour, then heated to 65° C. and stirred for 16 hours to afford I as the his mesylate salt. The salt was then recrystallized in a mixture of water and methanol in the presence of additional methanesulfonic acid.

A variety of palladium catalysts can be used during the Suzuki coupling step to form compounds 14 and 21. Suzuki coupling is a palladium mediated cross coupling reaction of an arylhalide, such as 9 and 20, with a boronic acid such as 10. Low valent, Pd(II) and Pd(0) catalysts may be used to prepare 14 and 21, including $PdCl_2(PPh_3)_2$, $Pd(t-Bu)_3$, $PdCl_2$ dppf $CH_2Cl_2$, $Pd(PPh_3)_4$, $Pd(OAc)/PPh_3$, $Cl_2Pd[(Pet_3)]_2$, $Pd(DIPHOS)_2$, $Cl_2Pd(Bipy)$, $[PdCl(Ph_2PCH_2PPh_2)]_2$, $Cl_2Pd[P(o-tol)_3]_2$, $Pd_2(dba)_3/P(o-tol)_3$, $Pd_2(dba)/P(furyl)_3$, $Cl_2Pd[P(furyl)_3]_2$, $Cl_2Pd(PMePh_2)_2$, $Cl_2Pd[P(4-F-Ph)_3]_2$, $Cl_2Pd[P(C_6F_6)_3]_2$, $Cl_2Pd[P(2-COOH-Ph)(Ph)_2]_2$, $Cl_2Pd[P(4-COOH-Ph)(Ph)_2]_2$, and encapsulated catalysts Pd EnCat™ 30, Pd EnCat™ TPP30, and Pd(II) EnCat™ BINAP30 (US 2004/0254066).

A variety of solid adsorbent palladium scavengers can be used to remove palladium after the Suzuki coupling step to form compounds 14 and 21. Exemplary embodiments of palladium scavengers described herein (Examples 10 and 17) include FLORISIL®, SILIABOUND® Thiol, and SILIABOND® Thiourea. Other palladium scavengers include silica gel, controlled-pore glass (TosoHaas), and derivatized low crosslinked polystyrene QUADRAPURE® AEA, QUADRAPURE® IMDAZ, QUADRAPURE® MPA, QUADRAPURE® TU (Reaxa Ltd., Sigma-Aldrich Chemical Co.).

Scheme 6

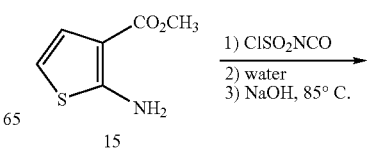

15

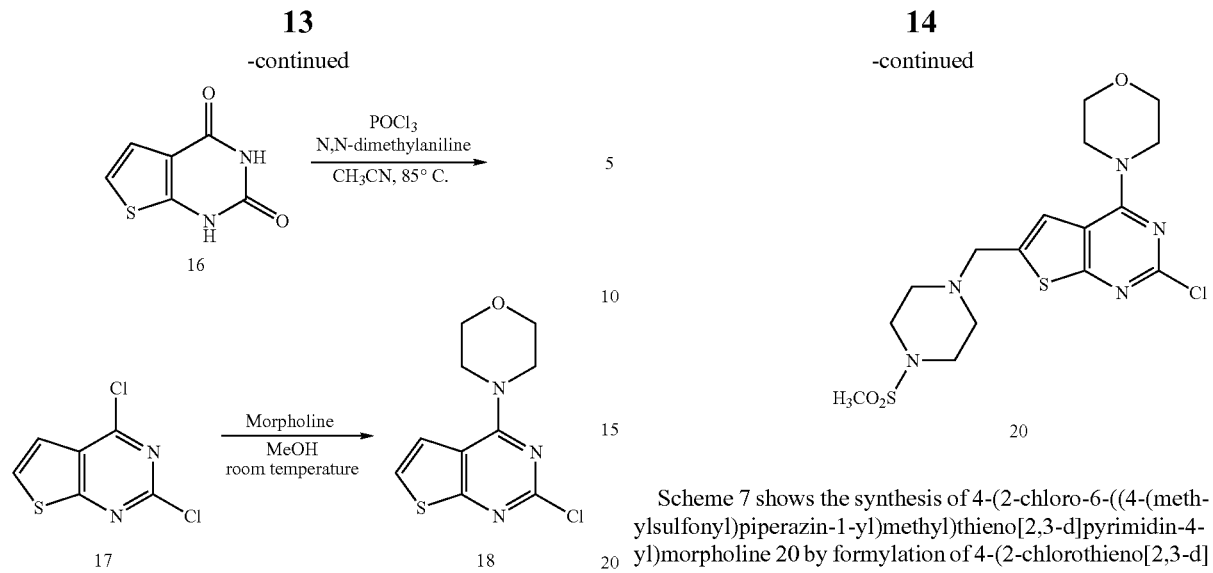

Scheme 6 shows the synthesis of 4-(2-chlorothieno[2,3-d]pyrimidin-4-yl)morpholine 18 starting by cyclization of methyl 2-amino-thiophenecarboxylate 15 (95 g) with chlorosulfonyl isocyanate at low temperature remains (−60° C. to −55° C.) to give thieno[2,3-d]pyrimidine-2,4(1H,3H)-dione 16. Phosphorous oxychloride was added slowly to a cold solution of thieno[2,3-d]pyrimidine-2,4(1H,3H)-dione 16 and N,N-dimethylaniline (0.75 equiv.) in acetonitrile while maintaining the temperature below 25° C. The mixture was then heated to 80-85° C. and stirred for 24 hours to afford dichlorothieno[2,3-d]pyrimidine 17. Morpholine (2.2 equiv.) was added to a solution of 2,4-dichlorothieno[2,3-d]pyrimidine 17 in methanol and stirred at ambient temperature for 1 h to give 18.

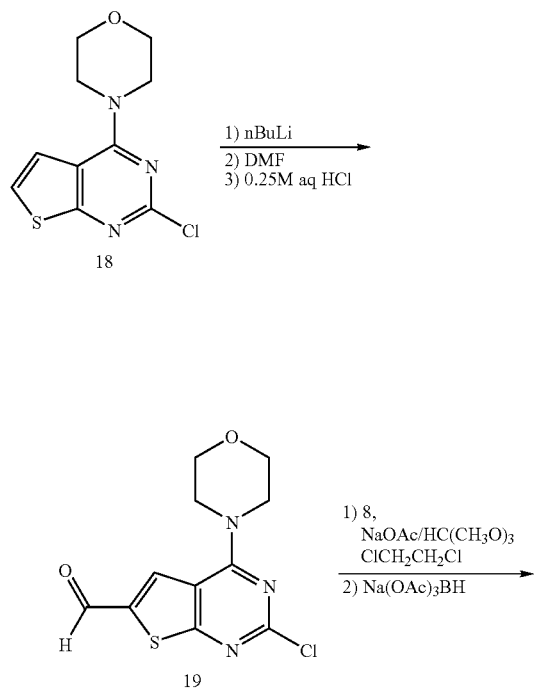

Scheme 7 shows the synthesis of 4-(2-chloro-6-((4-(methylsulfonyl)piperazin-1-yl)methyl)thieno[2,3-d]pyrimidin-4-yl)morpholine 20 by formylation of 4-(2-chlorothieno[2,3-d]pyrimidin-4-yl)morpholine 18 in THF at −78° C. with n-BuLi in hexanes (1.2 equiv.). The resulting slurry was allowed to warm up to −60° C., cooled to −78° C. and DMF (1.5 equiv.) was added slowly to afford 2-chloro-4-morpholinothieno[2,3-d]pyrimidine-6-carbaldehyde 19. To a suspension of 19, 4-(methylsulfonyl)piperazin-1-ium chloride 8 (alternatively named as 1-(methylsulfonyl)piperazine hydrochloride, 1.45 equiv.) and anhydrous sodium acetate in 1,2-dichloroethane was added trimethyl orthoformate (10 equiv.). The slurry was stirred at ambient temperature for at least 6 hours, then sodium triacetoxyborohydride was added and the reaction was stirred for 24 hours to give 20.

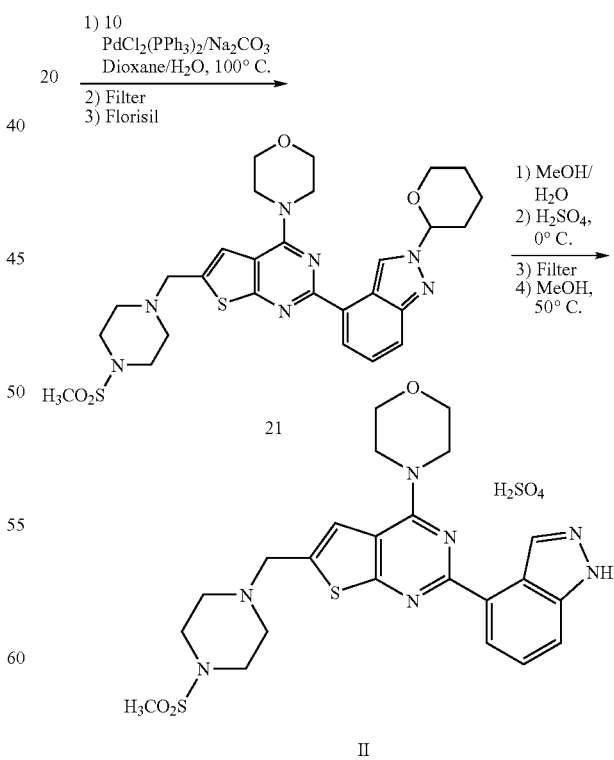

Scheme 8 shows the synthesis of 4-(2-(1H-Indazol-4-yl)-6-((4-(methylsulfonyl)piperazin-1-yl)methyl)thieno[2,3-d]

pyrimidin-4-yl)morpholine II sulfate salt starting with Suzuki coupling of 4-(2-chloro-6-((4-(methylsulfonyl)piperazin-1-yl)methyl)thieno[2,3-d]pyrimidin-4-yl)morpholine 20 in 1,4-dioxane with 2-(tetrahydro-2H-pyran-2-yl)-4-(4,4,5,5-tetramethyl-1,3,2-dioxaborolan-2-yl)-2H-indazole 10 (1.25 equiv.) and bis(triphenylphosphine)palladium (II) chloride (0.02 equiv.) in aqueous sodium carbonate. The mixture was heated to 88° C. and stirred for 14 hours. The reaction mixture was cooled, filtered, rinsed with water, and stirred with FLO-RISIL® (60-100 mesh, Sigma-Aldrich Chemical Company, Inc) in methylene chloride at ambient temperature for 5 hours. The mixture was filtered, rinsed with methylene chloride and ethyl acetate, and the filtrate and the rinse were combined and concentrated to give solid 21 with Pd content of 150 ppm. The solid was dissolved in methylene chloride and SILIABOND® Thiourea (Silicycle Inc) was added. The mixture was stirred for 5 hours, filtered, rinsed with methylene chloride and ethyl acetate. All the filtrate and the rinse were combined and concentrated to give 4-(6-((4-(methylsulfonyl)piperazin-1-yl)methyl)-2-(2-(tetrahydro-2H-pyran-2-yl)-2H-indazol-4-yl)thieno[2,3-d]pyrimidin-4-yl)morpholine 21 as a solid in 70% yield with Pd content<10 ppm), along with a minor amount of THP regioisomer 21A.

THP protected 21 was mixed with methanol and water, cooled to 0° C. and a cold solution of aqueous sulfuric acid (1.20 equiv.) was slowly added while maintaining the temperature below 10° C. The mixture was allowed to warm up to ambient temperature and stirred for 20 hours. The slurry was cooled to 5° C., filtered and rinsed with cold methanol. The cake was stirred in aqueous methanol at 50° C. for 3 hours, then cooled 0-5° C., filtered and rinsed with cold methanol to give a cake which was dried in a vacuum oven to afford II as a light yellow solid sulfate salt in 94% yield.

Methods of Separation

In the methods of preparing the compounds of this invention, it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point and molecular weight in distillation and sublimation, presence or absence of polar functional groups in chromatography, stability of materials in acidic and basic media in multiphase extraction, and the like. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. J. Org. Chem., (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

Pharmaceutical Formulations

In order to use a compound of this invention for the therapeutic treatment (including prophylactic treatment) of mammals including humans, it is normally formulated in accordance with standard pharmaceutical practice as a pharmaceutical composition. According to this aspect of the invention there is provided a pharmaceutical composition comprising a compound of this invention in association with a pharmaceutically acceptable diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

Pharmaceutical formulations of the compounds of the present invention may be prepared for various routes and types of administration. For example, a compound of Formula I or II having the desired degree of purity may optionally be mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment. The compound of this invention for use herein is preferably sterile. In particular, formulations to be used for in vivo administration must be sterile. Such sterilization is readily accomplished by filtration through sterile filtration membranes. The compound ordinarily can be stored as a solid composition, a lyophilized formulation or as an aqueous solution.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations of Formula I and II compounds may be prepared. Suitable examples of sustained-release preparations include semipermeable matrices of solid hydrophobic polymers containing a Formula I or II compound, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a Formula I or II compound suitable for oral administration may be prepared as discrete units such as pills, capsules, cachets or tablets each containing a predetermined amount of a Formula I or II compound.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula I or II intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Aqueous suspensions of Formula I or II compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula I or II may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

EXAMPLES

In order to illustrate the invention, the following examples are included. However, it is to be understood that these examples do not limit the invention and are only meant to suggest a method of practicing the invention. Persons skilled in the art will recognize that the chemical reactions described may be readily adapted to alternative methods for preparing the compounds of this invention which are deemed to be within the scope of this invention.

In the examples described below, unless otherwise indicated all temperatures are set forth in degrees Celsius (° C.). Reagents were purchased from commercial suppliers such as Sigma-Aldrich Chemical Company, and were used without further purification unless otherwise indicated.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted on a Biotage system (Manufacturer: Dyax Corporation) having a silica gel column or on a silica SEP PAK® cartridge (Waters). $^1$H NMR spectra were obtained in deuterated $CDCl_3$, $d_6$-DMSO, $CH_3OD$ or $d_6$-acetone solutions (reported in ppm), using chloroform as the reference standard (7.25 ppm). When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Example 1

Thieno[3,2-d]pyrimidine-2,4(1H,3H)-dione 2

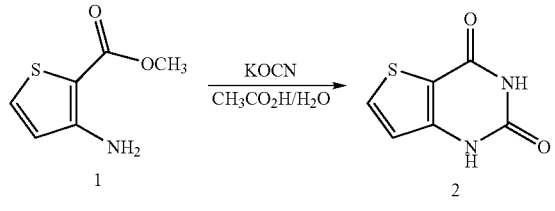 [SMILES: COC(=O)c1sccc1N ; "KOCN" ; O=c1[nH]c(=O)c2sccc2[nH]1]

To a mixture of methyl 3-amino-thiophenecarboxylate 1 (850 g, 5.41 mol, 1.0 equiv.), acetic acid (6 L) and water (5 L), a solution of potassium cyanate (KOCN, 1316 g, 16.22 mole, 3.0 equiv.) in water (3.2 L) was added slowly over a period of 1 hour. The resulting mixture was stirred at the ambient temperature for 20 hour, filtered and rinsed with water (4 L). The cake was charged to a suitably sized reactor and 2 M aqueous sodium hydroxide solution (14 L) was added. The slurry was stirred for 2 hours and LCMS confirmed the formation of the desired product. The mixture was cooled to 10° C. and 3 M aqueous hydrochloric acid (~11 L) was added until pH=5.0-6.0 (by pH paper). The slurry was filtered, rinsed with water (6 L), dried in vacuum oven at 50° C. for 24 hours to afford thieno[3,2-d]pyrimidine-2,4(1H,3H)-dione 2 as an off-white solid (834 g, 92%). $^1$H NMR (400 MHz, DMSO-$d_6$) δ 6.90 (d, J=5.2 Hz, 1H), 8.10 (d, J=5.2 Hz, 1H), 5.40-5.55 (br s, 2H). LCMS (ESI pos) m/e 169 (M+1).

Example 2

2,4-Dichlorothieno[3,2-d]pyrimidine 3

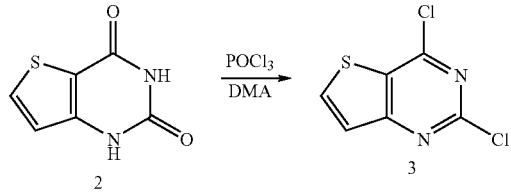 [SMILES: O=c1[nH]c(=O)c2sccc2[nH]1 ; "POCl3" ; Clc1nc(Cl)c2sccc2n1]

Phosphorous oxychloride (299 ml, 3.27 mol, 5.0 equiv.) was added slowly to a cold solution of thieno[3,2-d]pyrimidine-2,4(1H,3H)-dione 2 (110 g, 0.654 mol, 1.0 equiv.) and N,N-dimethylaniline (62 ml, 0.491 mol, 0.75 equiv.) in acetonitrile (550 ml) while maintaining the temperature below 20° C. The mixture was then heated to 80-85° C. and stirred for 24 hours. LCMS indicated that the reaction was complete. The reaction mixture was cooled to 15° C., and then poured slowly onto a mixture of ice and cold water (1.0 L). The resulting slurry was filtered, rinsed with cold water (300 ml). The cake was dried in vacuum oven at 40° C. for 24 hours to afford 2,4-dichlorothieno[3,2-d]pyrimidine 3 as an off-white solid (93.4 g, 67% yield). $^1$H NMR (400 MHz, DMSO-$d_6$) δ 7.56 (d, J=5.5 Hz, 1H), 8.76 (d, J=5.5 Hz, 1H). LCMS (ESI pos) m/e 205 (M+1).

Example 3

4-(2-Chlorothieno[3,2-d]pyrimidin-4-yl)morpholine 4

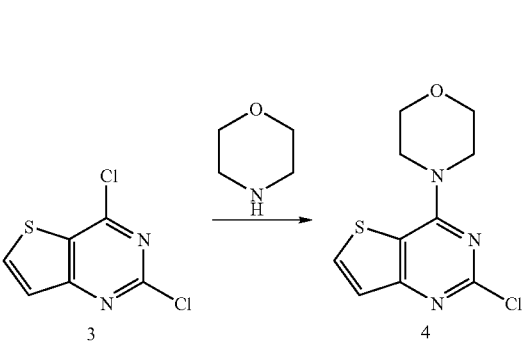 [SMILES: Clc1nc(Cl)c2sccc2n1 ; C1COCCN1 ; Clc1nc(N2CCOCC2)c2sccc2n1]

Morpholine (87 ml, 1.00 mol, 2.2 equiv.) was added to a solution of 2,4-dichloro-thieno[3,2-d]pyrimidine 3 (93.4 g, 0.456 mol, 1.0 equiv.). The reaction mixture was stirred at ambient temperature for 1 h and the resulting slurry was filtered, rinsed with water (500 ml). The cake was dried in a vacuum oven at 40° C. for 24 hours to give 4-(2-chlorothieno[3,2-d]pyrimidin-4-yl)morpholine 4 as an off-white solid (109 g, 94% yield). $^1$H NMR (400 MHz, DMSO-$d_6$) δ 3.74 (t, J=4.9 Hz, 4H), 3.90 (t, J=4.9 Hz, 4H), 7.40 (d, J=5.6 Hz, 1H), 8.30 (d, J=5.6 Hz, 1H). LCMS (ESI pos) m/e 257 (M+1).

Example 4

2-Chloro-4-morpholinothieno[3,2-d]pyrimidine-6-carbaldehyde 5

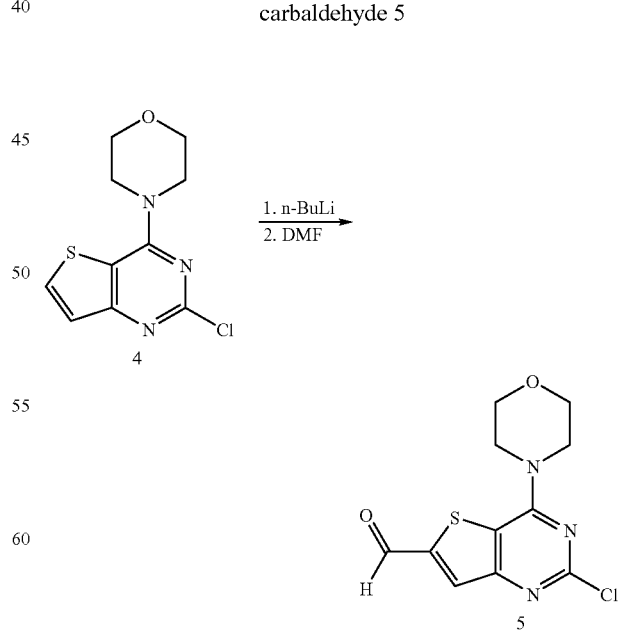

To a suspension of 4-(2-chlorothieno[3,2-d]pyrimidin-4-yl)morpholine 4 (50 g, 195 mmol, 1.0 equiv.) in THF (anhydrous, 800 ml) at −78° C. was added slowly 2.5 M solution of n-BuLi in hexanes (93.9 ml, 234.6 mmol, 1.2 equiv.). The resulting slurry was allowed to warm up to −60° C. and a clear brown solution was observed. The solution was then cooled to −78° C. and DMF (anhydrous, 22.7 ml, 293 mmol, 1.5 equiv.) was added slowly. The resulting solution was stirred at −78° C. for 0.5 hour, then warmed up slowly to 0° C. over a period of 1-1.5 hours. The solution was then poured slowly to a mixture of 0.25 M aq. hydrochloric acid (1.65 L) and ice water (800 ml). The resulting slurry was stirred at 0-10° C. for 0.5 hour, filtered and rinsed with cold water (200 ml). The cake was dried in vacuum oven at 40° C. for 24 hours to afford 2-chloro-4-morpholinothieno[3,2-d]pyrimidine-6-carbaldehyde 5 as a light yellow solid (54.9 g, 99% yield). $^1$H NMR (400 MHz, DMSO-$d_6$) δ 3.76 (t, J=4.9 Hz, 1H), 3.95 (t, J=4.9 Hz, 4H), 8.28 (s, 1H), 10.20 (s, 1H). LCMS (ESI pos) m/e 285 (M+1).

Example 5

4-(Methylsulfonyl)piperazin-1-ium chloride 8

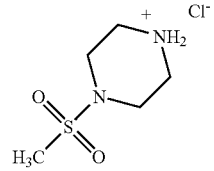

Methanesulfonyl chloride (34.38 ml, 443 mmol, 1.1 equiv.) was added slowly to a solution of 1-(tert-butoxycarbonyl)piperazine 6 (BOC-piperazine, 75 g, 403 mmol, 1.0 equiv.) and triethylamine (67.4 ml, 483 mmol, 1.2 equiv.) in methylene chloride (750 ml) while maintaining the internal temperature below 20° C. The solution was stirred at ambient temperature for 24 hours. The solution was poured onto a mixture of ice and water (1.5 L). The phases were separated and the aq. phase was extracted with methylene chloride (800 ml×2). The organic phases were combined, dried over MgSO$_4$, filtered and concentrated to give tert-butyl 4-(methylsulfonyl)piperazine-1-carboxylate 7 as an off-white solid (105 g). $^1$H NMR (400 MHz, CDCl$_3$) δ 1.45 (s, 9H), 2.75 (s, 3H), 3.15 (m, 4H), 3.50 (m, 4H).

A 4M hydrogen chloride solution in 1,4-dioxane (1.2 L) was added slowly to a cold solution of tert-butyl 4-(methylsulfonyl)piperazine-1-carboxylate 7 (105 g) in methylene chloride (1.1 L) while maintaining the internal temperature below 20° C. The solution was stirred for 20 hours and $^1$H NMR indicated that the reaction was complete. The resulting slurry was filtered and rinsed with methylene chloride (300 ml). The cake was dried in a vacuum oven at 50° C. for 20 hours to afford 4-(methylsulfonyl)piperazin-1-ium chloride 8 as a white solid (78.4 g, 97% yield over 2 steps). $^1$H NMR (400 MHz, CDCl$_3$) δ 3.00 (s, 3H), 3.17 (m, 4H), 3.38 (m, 4H), 9.45 (br s, 2H).

Example 6

4-(2-Chloro-6-((4-(methylsulfonyl)piperazin-1-yl)methyl)thieno[3,2-d]pyrimidin-4-yl)morpholine 9

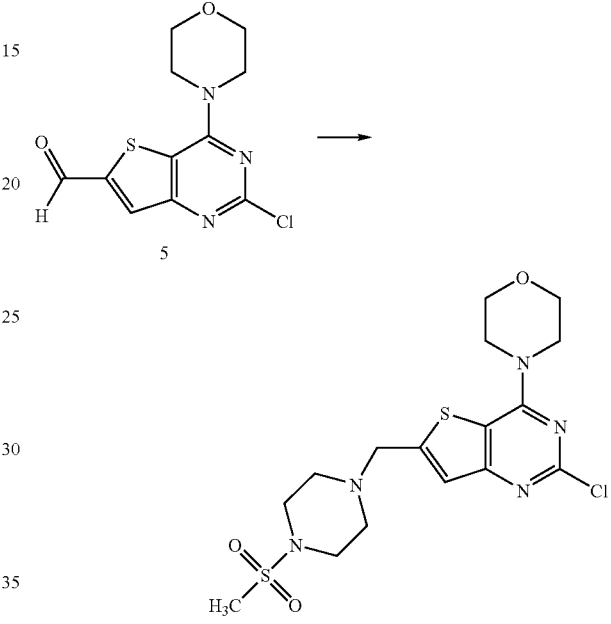

To a suspension of 2-chloro-4-morpholinothieno[3,2-d]pyrimidine-6-carbaldehyde 5 (20.6 g, 72.6 mmol, 1.0 equiv.), 4-(methylsulfonyl)piperazin-1-ium chloride 8 (18.9 g, 94.4 mmol, 1.30 equiv.) and sodium acetate (anhydrous powder, 7.74 g, 94.4 mmol, 1.30 equiv.) in 1,2-dichloroethane (anhydrous, 412 ml) was added trimethyl orthoformate (79.5 ml, 726 mmol, 10 equiv.). The slurry was stirred at ambient temperature for at least 6 hours. Sodium triacetoxyborohydride (assay>90%, 20.5 g, 87.1 mmol, 1.2 equiv.) was added and the reaction was stirred for 24 hours. LC/MS indicated that the reaction was complete. The reaction was quenched with water (1.0 L) and methylene chloride (1.0 L). The phases were separated and the organic phase was dried over MgSO$_4$, filtered and concentrated to give a yellow solid (35 g). The crude solid was then stirred in ethyl acetate (500 ml) at 80° C. for 2 hours. The slurry was cooled to 30-40° C., filtered and rinsed with ethyl acetate (50 ml). The cake was dried in vacuum oven at 45° C. to give 4-(2-chloro-6-((4-(methylsulfonyl)piperazin-1-yl)methyl)thieno[3,2-d]pyrimidin-4-yl) morpholine 9 as an off-white solid (24 g, 75% yield). $^1$H NMR (400 MHz, DMSO-$d_6$) δ 2.53-2.60 (m, 4H), 2.90 (s, 3H), 3.09-3.19 (m, 4H), 3.73 (t, J=4 Hz, 4H), 3.89 (t, J=4 Hz, 4H), 3.91 (s, 2H), 7.31 (s, 1H). LCMS (ESI pos) m/e 432 (M+1).

Example 7

4-Chloro-1H-indazole 12

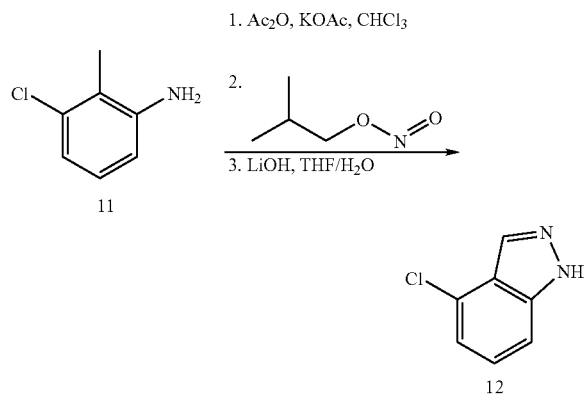

To a 250 ml flask with stir bar was added 3-chloro-2-methylaniline 11 (8.4 ml, 9.95 g, 70.6 mmol), potassium acetate (8.3 g, 84.7 mmol) and chloroform (120 ml). This mixture was cooled to 0° C. with stirring. To the cooled mixture was added acetic anhydride (20.0 ml, 212 mmol) drop wise over 2 minutes. The reaction mixture was warmed to 25° C. and stirred for 1 hour. At this point, the reaction was heated to 60° C. Isoamyl nitrite (18.9 ml, 141 mmol) was added and the reaction was stirred overnight at 60° C. Once complete, water (75 ml) and THF (150 ml) were added and the reaction was cooled to 0° C. Lithium hydroxide (LiOH, 20.7 g, 494 mmol) was added and the reaction was stirred at 0° C. for 3 hours. Water (200 ml) was added and the product was extracted with EtOAc (300 ml, 100 ml). The organic layers were combined, dried with MgSO$_4$ and concentrated to yield 4-chloro-1H-indazole 12 as an orange solid (11.07 g (100%). $^1$H NMR (400 MHz, CDCl$_3$) δ 8.18 (d, J=1 Hz, 1H), 7.33 (d, J=8 Hz 1H), 7.31 (t, J=7 Hz, 1H), 7.17 (dd, J=7 Hz, 1 Hz 1H). LCMS (ESI pos) m/e 153 (M+1).

Example 8

4-Chloro-2-(tetrahydro-2H-pyran-2-yl)-2H-indazole 13

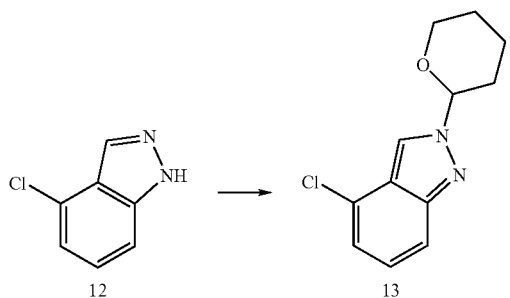 [SMILES: Clc1cccc2[nH]ncc12 ; Clc1cccc2nn(C3CCCCO3)cc12]

To a 1 L flask with mechanical stirrer was added 4-chloro-1H-indazole 12 (75.0 g, 0.492 mol), pyridinium p-toluenesulfonate (1.24 g, 4.92 mmol), CH$_2$Cl$_2$ (500 ml) and 3,4-dihydro-2H-pyran (98.6 ml, 1.08 mol). With stirring, this mixture was heated to 45° C. for 16 hours. Analysis of reaction mixture shows production of both isomers of product. Cooled reaction to 25° C. and added CH$_2$Cl$_2$ (200 ml). Washed the solution with water (300 ml) and saturated NaHCO$_3$ (250 ml). Dried the organics with MgSO$_4$ and concentrated to dryness. Purified the crude product by dissolving in EtOAc/Hexanes (4:6, 1 L) and adding SiO$_2$ (1.2 L). The mixture was filtered and the cake was washed with EtOAc/Hexanes (4:6, 2 L). The organics were concentrated to yield 4-chloro-2-(tetrahydro-2H-pyran-2-yl)-2H-indazole 13 as an orange solid (110.2 g, 95%) and a minor amount (about 10%) of the THP regioisomer, 4-chloro-1-(tetrahydro-2H-pyran-2-yl)-1H-indazole. Isomer 1: $^1$H NMR (400 MHz, CDCl$_3$) δ 8.10 (d, J=1 Hz, 1H), 7.50 (dd, J=9 Hz, 1 Hz 1H), 7.29 (dd, J=9 Hz, 8 Hz 1H), 7.15 (dd, J=8 Hz, 1 Hz 1H) 5.71 (dd, J=9 Hz, 3 Hz 1H) 4.02 (m, 1H) 3.55 (m, 1H) 2.51 (m, 1H) 2.02 (m, 2H) 1.55 (m, 3H). LCMS (ESI pos) m/e 237 (M+1); Isomer 2: $^1$H NMR (400 MHz, CDCl$_3$) δ 8.25 (d, J=1 Hz, 1H), 7.62 (dd, J=9 Hz, 1 Hz 1H), 7.20 (dd, J=9 Hz, 8 Hz 1H), 7.06 (dd, J=8 Hz, 1 Hz 1H) 5.69 (dd, J=9 Hz, 3 Hz 1H) 4.15 (m, 1H) 3.80 (m, 1H) 2.22 (m, 2H) 2.05 (m, 1H) 1.75 (m, 3H). LCMS (ESI pos) m/e 237 (M+1).

Example 9

2-(Tetrahydro-2H-pyran-2-yl)-4-(4,4,5,5-tetramethyl-1,3,2-dioxaborolan-2-yl)-2H-indazole 10

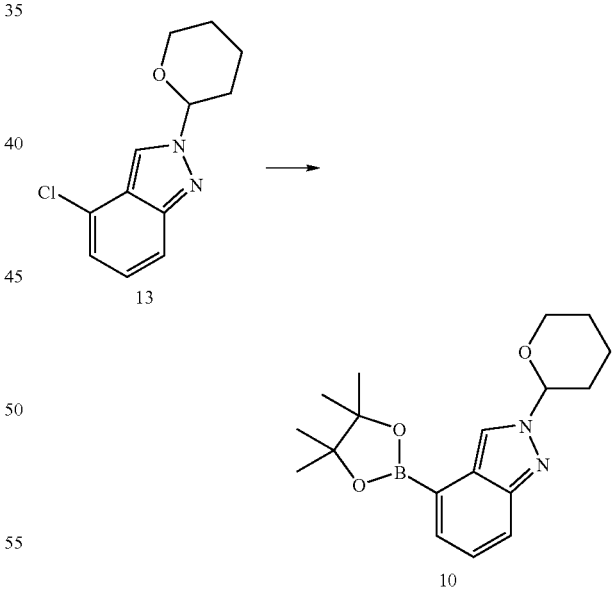

To a 500 ml flask with stir bar was added 4-chloro-2-(tetrahydro-2H-pyran-2-yl)-2H-indazole 13 (10.0 g, 42.2 mmol), DMSO (176 ml), PdCl$_2$(PPh$_3$)$_2$ (6.2 g, 8.86 mmol), tricyclohexylphosphine (0.47 g, 1.69 mmol), bis(pinacolato)diboron (16.1 g, 63.4 mmol) and potassium acetate (12.4 g, 0.127 mol). With stirring, the mixture was heated to 130° C. for 16 hours. The reaction was cooled to 25° C. and EtOAc (600 ml) was added and washed with water (2×250 ml). The organics were dried with MgSO$_4$ and concentrated to dryness.

The crude product was purified by SiO₂ plug (120 g), eluting with 10% EtOAc/Hexanes (1 L) and 30% EtOAc/Hexanes (1 L). The filtrate was concentrated to give 2-(tetrahydro-2H-pyran-2-yl)-4-(4,4,5,5-tetramethyl-1,3,2-dioxaborolan-2-yl)-2H-indazole 10 (13.9 g, 100%) as a 20% (wt/wt) solution in ethyl acetate. $^1$H NMR shows the presence of about 20% (wt/wt) bis(pinacolato)diboron, and a minor amount (about 10%) of the THP regioisomer, 1-(tetrahydro-2H-pyran-2-yl)-4-(4,4,5,5-tetramethyl-1,3,2-dioxaborolan-2-yl)-1H-indazole. $^1$H NMR (400 MHz, CDCl₃) δ 8.37 (s, 1H), 7.62 (dd, J=14 Hz, 2 Hz 1H), 7.60 (dd, J=7 Hz, 1 Hz 1H), 7.31 (dd, J=8 Hz, 7 Hz 1H) 5.65 (dd, J=9 Hz, 3 Hz 1H) 4.05 (m, 1H) 3.75 (m, 1H) 2.59 (m, 1H) 2.15 (m, 1H) 2.05 (m, 1H) 1.75 (m, 3H) 1.34 (s, 12H). LCMS (ESI pos) m/e 245 (M+1).

Example 10

4-(6-((4-(Methylsulfonyl)piperazin-1-yl)methyl)-2-(2-(tetrahydro-2H-pyran-2-yl)-2H-indazol-4-yl)thieno[3,2-d]pyrimidin-4-yl)morpholine 14

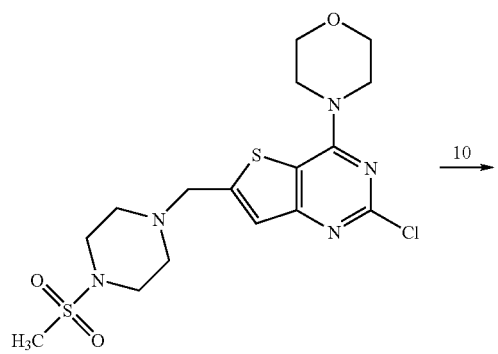

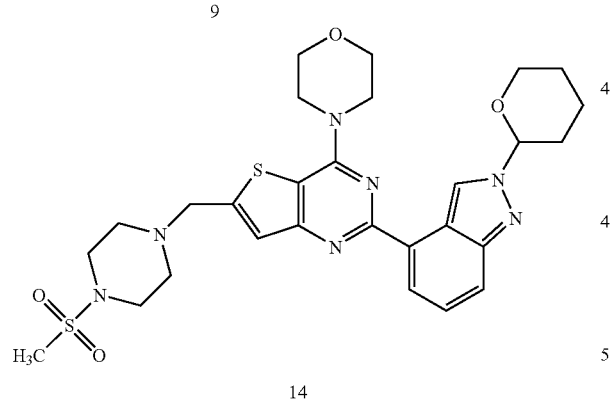

To a solution of 4-(2-chloro-6-((4-(methylsulfonyl)piperazin-1-yl)methyl)thieno[3,2-d]pyrimidin-4-yl)morpholine 9 (96.5 g, 223 mmol, 1.0 equiv.) in 1,4-dioxane (1.75 L) was added water (772 ml), sodium carbonate (47.4 g, 447 mmol, 2.0 equiv.) and 2-(tetrahydro-2H-pyran-2-yl)-4-(4,4,5,5-tetramethyl-1,3,2-dioxaborolan-2-yl)-2H-indazole 10 (73 w/w %, 150.7 g, 325 mmol, 1.5 equiv.). The mixture was degassed for three times. Bis(triphenylphosphine)palladium (II) chloride (6.28 g, 9.94 mmol, 0.04 equiv.) was added and the resulting slurry was degassed for 4 times. The mixture was heated to 88° C. and stirred for 14 hours. The reaction mixture was cooled to 50° C., concentrated under vacuum to half of the total volume and then cooled to 15° C., and acetonitrile (900 ml) was added. After 2 hours of agitation, the resulting slurry was cooled to −5° C., filtered and rinsed with acetonitrile (40 ml), water (90 ml), and acetonitrile (40 ml). The cake was dried in a vacuum oven at 50° C. for 24 hours to afford a brown-yellow solid (140 g, the Pd content: 2000 ppm). The cake was dissolved in methylene chloride (1930 ml) and FLORISIL® (60-100 mesh, 193 g, purchased from Aldrich Chemical Company, Inc) was then added. The slurry was stirred at the ambient temperature for a minimum of 5 hours and SILIABOUND®Thiol (28 g) was added. The mixture was stirred at ambient temperature for a minimum of 12 hours, filtered and rinsed with methylene chloride (2 L), followed by a mixture of methylene chloride (2 L) and ethyl acetate (2 L). All the filtrate and the rinse were combined and concentrated to give 4-(6-((4-(methylsulfonyl)piperazin-1-yl)methyl)-2-(2-(tetrahydro-2H-pyran-2-yl)-2H-indazol-4-yl)thieno[3,2-d]pyrimidin-4-yl)morpholine 14 as an off-white solid (93 g) with Pd content of less than 20 ppm, and containing a minor amount of THP regioisomer 14A. $^1$H NMR (300 MHz, CDCl₃) δ 1.20-4.30 (br, 8H), 2.61-2.64 (m, 4H), 2.74 (s, 3H), 3.23-3.26 (m, 4H), 3.83-3.86 (m, 6H), 3.99-4.02 (m, J=4.15 Hz, 4H), 5.66-5.70 (m, 1H), 7.32 (s, 1H), 7.32-7.37 (dd, 8.6 Hz, 7.1 Hz, 1H), 7.77-7.80 (d, 8.6 Hz, 1H), 8.22-8.25 (d, 6.99 Hz, 1H), 9.04 (s, 1H). LCMS (ESI pos) m/e 598 (M+1).

Example 11

4-(2-(1H-Indazol-4-yl)-6-((4-(methylsulfonyl)piperazin-1-yl) methyl)thieno[3,2-d]pyrimidin-4-yl)morpholine I

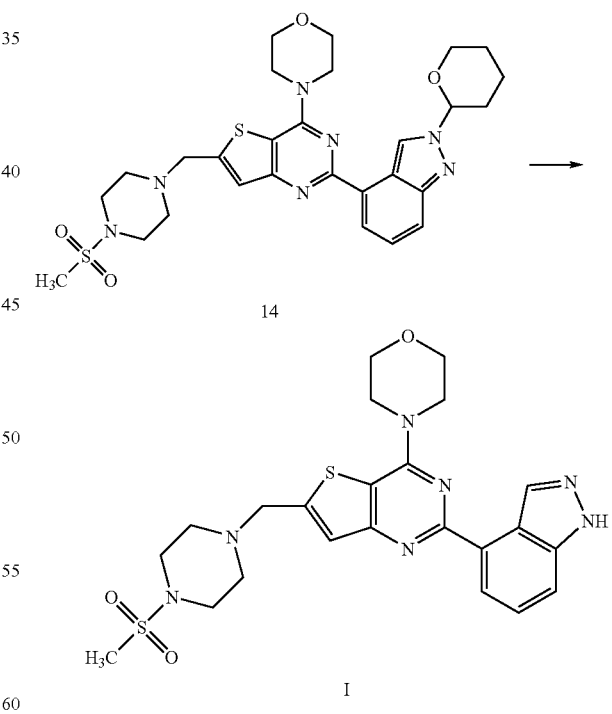

4-(6-((4-(Methylsulfonyl)piperazin-1-yl)methyl)-2-(2-(tetrahydro-2H-pyran-2-yl)-2H-indazol-4-yl)thieno[3,2-d] pyrimidin-4-yl)morpholine 14 (200 g, 0.3346 mole) was charged to a suitably sized reactor under nitrogen, followed by methanol (3.0 L) and water (0.16 L). Methanesulfonic acid (160.8 g, 1.673 mole, 5.00 equiv.) was slowly added to the reactor (a mild exotherm is observed). The slurry was stirred at ambient temperature for 1 hour, then heated to 65° C. and stirred for 16 hours. A sample was taken from the reactor and submitted for HPLC analysis. HPLC indicated the content of the residual starting material was 0.5% (specification<1%). The reaction mixture was cooled to 0-5° C. and stirred for >3 hours, filtered and rinsed with cold methanol (0-5° C., 600 ml). The cake was transferred to a sizable reactor, followed by ethyl acetate (1 L) and methyl-tert-butyl ether (2 L). The resulting slurry was stirred at ambient temperature for >4 hours, filtered and rinsed with methyl-tert-butyl ether (200 ml). The cake was dried in a vacuum oven at 55° C. for at least 12 hours to afford 4-(2-(1H-indazol-4-yl)-6-((4-(methylsulfonyl)piperazin-1-yl)methyl)thieno[3,2-d]pyrimidin-4-yl)morpholine I bis mesylate salt as an off-white solid (224 g).

The solid was transferred to a suitably sized reactor followed by the addition of water (1.34 L). The resulting mixture was heated to 30° C. to obtain a clear solution. The solution was then filtered through double in-line filters (1 micron and 0.45 micron) to remove any foreign material. The filtrate was concentrated at 55° C. under vacuum until approximately 80% of the water has been removed. Methanol (3.36 L) was added to the reactor through an in-line filter (0.45 micron) and the resulting mixture was cooled to 5° C. and methanesulfonic acid (60.5 g) was slowly added. After stirred at 5° C. for 30 minutes, the mixture was heated to 55° C. and stirred for a minimum of 16 hours. In-process XRPD (X-ray powder diffraction) and DSC (differential scanning calorimetry) confirmed the desired crystalline form and the slurry was cooled to 0° to 5° C. and stirred for a minimum of 3 hours, filtered, and rinsed with cold methanol (0° C. to 5° C., 0.47 L). The cake was transferred to a reactor of suitable size, followed by the addition of ethyl acetate (1.0 L) and tert-butylmethyl ether (2.0 L). The resulting slurry was stirred at ambient temperature for a minimum of 4 hours, filtered, and rinsed with tert-butylmethyl ether (1.50 wt). The cake was dried in a vacuum oven at 55° C. for a minimum of 12 hours to afford 4-(2-(1H-indazol-4-yl)-6-((4-(methylsulfonyl)piperazin-1-yl)methyl)thieno[3,2-d]pyrimidin-4-yl)morpholine I bis mesylate salt as an off-white solid (204 g, 87%). $^1$H NMR (300 MHz, DMSO-$d_6$) δ 2.40 (s, 6H), 3.02 (s, 3H), 3.01 (s, 3H), 3.00-3.87 (br, 8H), 3.88-3.89 (m, 4H), 4.10-4.12 (m, 4H), 4.77 (br, 2H), 7.52-7.57 (t, 7.8 Hz, 1H), 7.77-7.83 (t, 8.7 Hz, 2H), 8.14-8.16 (d, 7.17 Hz, 1H), 8.76 (s, 1H). LCMS (ESI pos) m/e 514 (M+1).

The product I bis mesylate was milled through a jet mill using nitrogen as the process gas. The milling conditions were as follows: Venturi pressure: 100 psi; mill pressure: 35 to 50 psi; and feed rate: 3.6 to 4.4 kg/hr. The typical recovery is 93% to 97%

Example 12

Thieno[2,3-d]pyrimidine-2,4(1H,3H)-dione 16

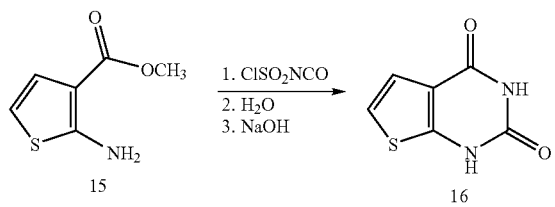 [SMILES: COC(=O)c1ccsc1N ; O=c1[nH]c(=O)c2ccsc2[nH]1]

A solution of methyl 2-amino-thiophenecarboxylate 15 (95 g) and dichloromethane (2.85 L) was cooled the to −60° C. and chlorosulfonyl isocyanate (89.81 g) was added at a rate such that the internal temperature remains at −60° C. to −55° C. The resulting mixture was then allowed to warm up to 20° C. and the complete consumption of starting material was confirmed by LCMS. The mixture was then concentrated to dryness via rotary evaporator and the solids was stirred in a 5 L flask with water (1.9 L) at 75° C. for one hour. The slurry was then cooled to 30° C. and a solution of 10 M NaOH (200 mL) was added. The mixture was heated to 85° C. and stirred for 20 min., then cool to room temperature. Conc. HCl was added until pH=1 and the mixture were stirred at ambient temperature for 18 hrs. The slurry was then filtered and rinsed with cold water (3×300 ml). The cake was dried in vacuum oven at 55° C. for 24 hours to afford thieno[2,3-d]pyrimidine-2,4(1H,3H)-dione 16 as an off-white solid (80.05 g, 79%). $^1$H NMR (400 MHz, DMSO-$d_6$) δ 7.08 (d, J=5.6 Hz, 1H), δ 7.12 (d, J=5.6 Hz, 1H). LCMS (ESI pos) m/e 169 (M+1). LCMS (ESI pos) m/e 169 (M+1).

Example 13

2,4-Dichlorothieno[2,3-d]pyrimidine 17

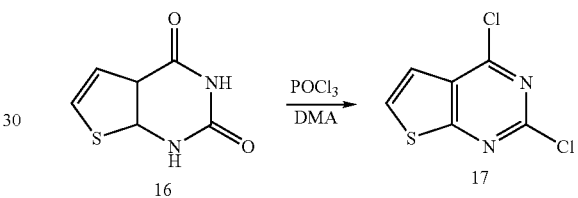

Phosphorous oxychloride (365 g, 2.38 mol, 5.0 equiv.) was added slowly to a cold solution of thieno[2,3-d]pyrimidine-2,4(1H,3H)-dione 16 (80 g, 0.476 mol, 1.0 equiv.) and N,N-dimethylaniline (42 g, 0.347 mol, 0.75 equiv.) in acetonitrile (400 ml) while maintaining the temperature below 25° C. The mixture was then heated to 80-85° C. and stirred for 24 hours. LCMS indicated that the reaction was complete. The reaction mixture was cooled to 15° C., then poured slowly onto a mixture of ice and cold water (1.0 L). The resulting slurry was filtered, rinsed with cold water (300 ml). The cake was dried in vacuum oven at 40° C. for 24 hours to afford dichlorothieno[2,3-d]pyrimidine 17 as an off-white solid (93.4 g, 67% yield). $^1$H NMR (400 MHz, DMSO-$d_6$) δ 7.62 (d, J=6.4 Hz, 1H), δ 8.16 (d, J=6.4 Hz, 1H). LCMS (ESI pos) m/e 205 (M+1).

Example 14

4-(2-chlorothieno[2,3-d]pyrimidin-4-yl)morpholine 18

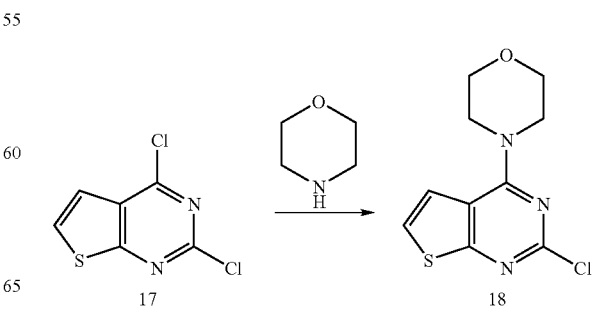

Morpholine (85.1, 0.977 mol, 2.2 equiv.) was added to a solution of 2,4-dichlorothieno[2,3-d]pyrimidine 17 (91 g, 0.444 mol, 1.0 equiv.). The reaction mixture was stirred at ambient temperature for 1 h and the resulting slurry was filtered, rinsed with water (500 ml). The cake was dried in vacuum oven at 55° C. for 24 hours to give 442-chlorothieno [2,3-d]pyrimidin-4-yl)morpholine 18 as an off-white solid (100.3 g, 88% yield). $^1$H NMR (400 MHz, DMSO-$d_6$) δ 3.736 (t, J=4.8 Hz, 4H), δ 3.897 (t, J=5.2 Hz, 4H), δ 7.658 (d, J=6.4 Hz, 1H), δ 7.682 (t, J=6.4 Hz, 4H δ). LCMS (ESI pos) m/e 257 (M+1).

Example 15

2-Chloro-4-morpholinothieno[2,3-d]pyrimidine-6-carbaldehyde 19

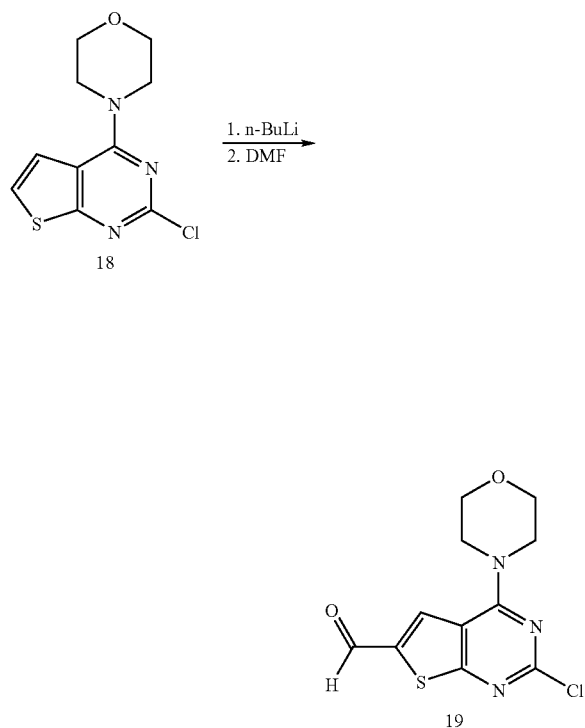

To a suspension of 4-(2-chlorothieno[2,3-d]pyrimidin-4-yl)morpholine 18 (90.2 g, 0.350 mol, 1.0 equiv.) in THF (anhydrous, 1400 ml) at −78° C. was added slowly 2.5 M solution of n-BuLi in hexanes (169 ml, 0.522 mol, 1.2 equiv.). The resulting slurry was allowed to warm up to −60° C. and a clear brown solution was observed. The solution was then cooled to −78° C. and DMF (anhydrous, 38.67 g, 0.530 mole, 1.5 equiv.) was added slowly. The resulting solution was stirred at −78° C. for 0.5 hour, and warmed up slowly to 0° C. over a period of 1-1.5 hours. The solution was then poured slowly to a mixture of 0.25 M aq. hydrochloric acid (3.0 L) and ice water (1.4 L). The resulting slurry was stirred at 0-10° C. for 0.5 hour, filtered and rinsed with cold water (0.5 L). The cake was dried in vacuum oven at 55° C. for 24 hours to afford 2-chloro-4-morpholinothieno[2,3-d]pyrimidine-6-carbaldehyde 19 as a light yellow solid (90.8 g, 91% yield). $^1$H NMR (400 MHz, DMSO-$d_6$) δ 3.778 (t, J=4.8 Hz, 4H), 3.990 (t, J=4.8 Hz, 4H), 8.756 (s, 1H), 10.022 (s, 1H). LCMS (ESI pos) m/e 285 (M+1).

Example 16

4-(2-Chloro-6-((4-(methylsulfonyl)piperazin-1-yl) methyl)thieno[2,3-d]pyrimidin-4-yl)morpholine 20

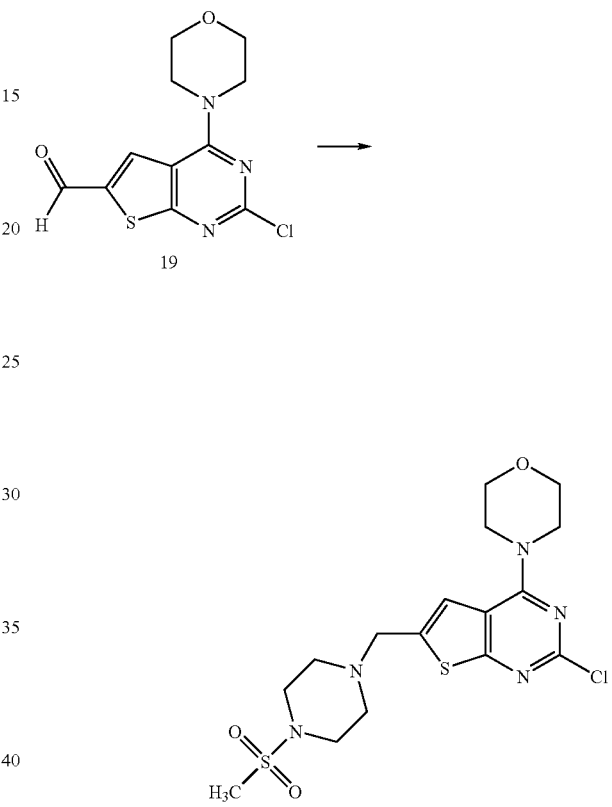

To a suspension of 2-chloro-4-morpholinothieno[2,3-d] pyrimidine-6-carbaldehyde 19 (90.8 g, 0.320 mol, 1.0 equiv.), 4-(methylsulfonyl)piperazin-1-ium chloride 8 (alternatively named as 1-(methylsulfonyl)piperazine hydrochloride, 92.3 g, 0.460 mol, 1.45 equiv.) and sodium acetate (anhydrous powder, 37.7 g, 0.460 mol, 1.45 equiv.) in 1,2-dichloroethane (anhydrous, 1.8 L) was added trimethyl orthoformate (340 g, 3.20 mol, 10 equiv.). The slurry was stirred at ambient temperature for at least 6 hours. Sodium triacetoxyborohydride (assay>90%, 101.3 g, 0.430 mol, 1.35 equiv.) was added and the reaction was stirred for 24 hours. LC/MS indicated that the reaction was complete. The reaction was quenched with water (4.4 L) and methylene chloride (4.4 L). The phases were separated and the organic phase was dried over MgSO$_4$, filtered and concentrated to give a yellow solid. The crude solid was then stirred in ethyl acetate (2.0 L) at 80° C. for 2 hours. The slurry was cooled to 30-40° C., filtered and rinsed with ethyl acetate (50 ml). The cake was dried in vacuum oven at 45° C. to give 4-(2-chloro-6-((4-(methylsulfonyl)piperazin-1-yl)methyl)thieno[2,3-d]pyrimidin-4-yl) morpholine 20 as an off-white solid (110.2 g, 80% yield). $^1$H NMR (400 MHz, DMSO-$d_6$) δ 2.52-2.55 (m, 4H), 2.89 (s, 3H), 3.12-3.14 (m, 4H), 3.73 (t, J=4.4 Hz, 4H), 3.81 (s, 2H), 3.86 (t, J=4.8 Hz, 4H), 7.59 (s, 1H). LCMS (ESI pos) m/e 432 (M+1).

Example 17

4-(6-((4-(Methylsulfonyl)piperazin-1-yl)methyl)-2-(2-(tetrahydro-2H-pyran-2-yl)-2H-indazol-4-yl)thieno[2,3-d]pyrimidin-4-yl)morpholine 21

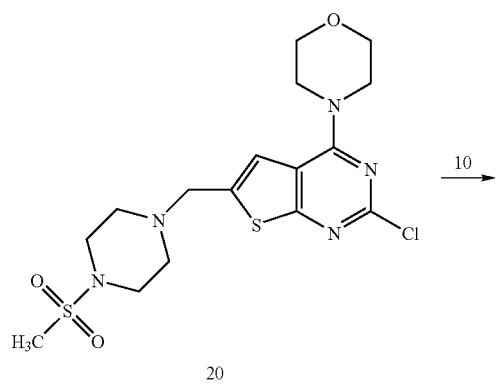

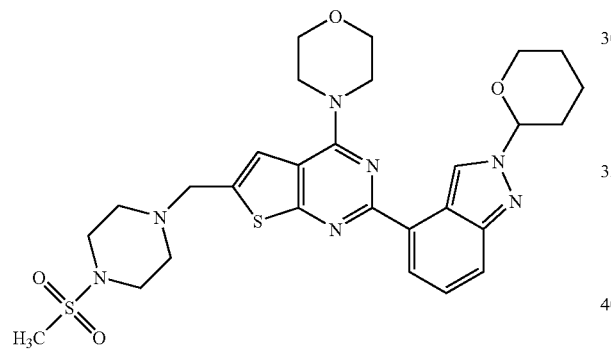

To a solution of 4-(2-chloro-6-((4-(methylsulfonyl)piperazin-1-yl)methyl)thieno[2,3-d]pyrimidin-4-yl)morpholine 20 (110 g, 0.250 mol, 1.0 equiv.) in 1,4-dioxane (1.98 L) was added water (0.88 L), sodium carbonate (54.1 g, 0.50 mol, 2.0 equiv.) and 2-(tetrahydro-2H-pyran-2-yl)-4-(4,4,5,5-tetramethyl-1,3,2-dioxaborolan-2-yl)-2H-indazole 10 (50 w/w %, 209.4 g, 0.310 mol, 1.25 equiv.). The mixture was degassed for three times. Bis(triphenylphosphine)palladium (II) chloride (3.57 g, 0.005 mol, 0.02 equiv.) was added and the resulting slurry was degassed for 4 times. The mixture was heated to 88° C. and stirred for 14 hours. The reaction was complete by LCMS and the reaction mixture was cooled to the ambient temperature, filtered and rinsed with water (2.0 L).

The crude product was then stirred with FLORISIL® (60-100 mesh, 101 g, purchased from Aldrich Chemical Company, Inc) in methylene chloride (2 L) at ambient temperature for at least 5 hours, then filtered, rinsed with methylene chloride (3 L), followed by a mixture of methylene chloride (2 L) and ethyl acetate (2 L). All the filtrate and the rinse were combined and concentrated to give a solid (110 g, the Pd content: 150 ppm). The solid was dissolved in methylene chloride and SILIABOND® Thiourea (50 g, Silicycle Inc., Crawford Scientific Ltd.) was added. The mixture was stirred for 5 hours, filtered, rinsed with methylene chloride (3 L), followed by a mixture of methylene chloride (2 L) and ethyl acetate (2 L). All the filtrate and the rinse were combined and concentrated to give 4-(6-((4-(methylsulfonyl)piperazin-1-yl)methyl)-2-(2-(tetrahydro-2H-pyran-2-yl)-2H-indazol-4-yl)thieno[2,3-d]pyrimidin-4-yl)morpholine 21 as a solid (98 g, Pd content: <10 ppm, 70%) along with a minor amount of THP regioisomer 21A. $^1$H NMR (300 MHz, CDCl$_3$) δ 1.20-2.40 (br, 6H), 2.66-2.69 (m, 4H), 2.81 (s, 3H), 3.28-3.31 (m, 4H), 3.78-3.86 (m, 3H), 3.91-3.94 (m, J=4.15 Hz, 4H), 3.97-4.00 (m, J=4.21, 4H), 4.15-4.19 (d, 1H), 5.74-5.78 (dd, 8.9 Hz, 3.2 Hz, 1H), 7.16 (s, 1H), 7.39-7.44 (dd, 8.6 Hz, 7.1 Hz, 1H), 7.84-7.87 (d, 8.7 Hz, 1H), 8.30-8.32 (dd, 7.08 Hz, 0.72 Hz, 1H), 9.11 (s, 1H). LCMS (ESI pos) m/e 598 (M+1).

Example 18

4-(2-(1H-Indazol-4-yl)-6-((4-(methylsulfonyl)piperazin-1-yl)methyl)thieno[2,3-d]pyrimidin-4-yl)morpholine II

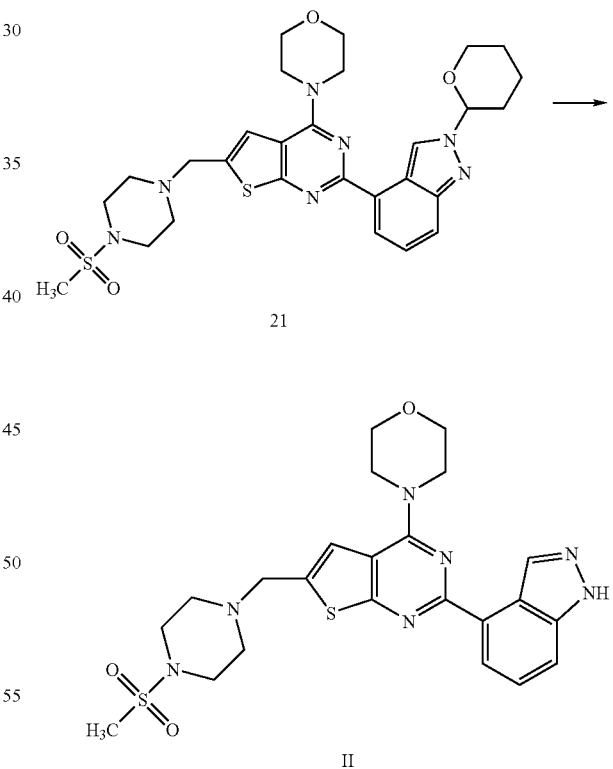

4-(6-((4-(Methylsulfonyl)piperazin-1-yl)methyl)-2-(2-(tetrahydro-2H-pyran-2-yl)-2H-indazol-4-yl)thieno[2,3-d]pyrimidin-4-yl)morpholine 21 (500 g, 0.836 mole) was charged to a sizable reactor, followed by methanol (9.5 L) and water (250 ml). The resulting slurry was cooled to 0° C. and stirred for 0.5 h. A cold solution of concentrated sulfuric acid (H$_2$SO$_4$, 5.54 ml, assay 95-98%, 1.004 mole, 1.20 equiv.) and water (250 ml) was slowly added while maintaining the temperature below 10° C. The mixture was allowed to warm up to the ambient temperature and stirred for 20 hours. The slurry was cooled to 5° C., filtered and rinsed with cold methanol (2 L). The cake was charged to a reactor and stirred in a mixture of methanol (9.5 L) and water (25 ml) at 50° C. for 3 hours. The slurry was cooled 0-5° C., filtered and rinsed with cold methanol (2 L). The cake was dried in a vacuum oven at 50° C. for 24 hours to afford 4-(2-(1H-Indazol-4-yl)-6-((4-(methylsulfonyl)piperazin-1-yl)methyl)thieno[2,3-d]pyrimidin-4-yl)morpholine II sulfate salt as a light yellow solid (482 g, 94%). $^1$H NMR (300 MHz, DMSO-d$_6$) δ 3.00-4.00 (br, 8H), 3.01 (s, 3H), 3.85-3.87 (m, 4H), 4.00-4.02 (m, 4H), 4.69 (s, 2H), 7.46-7.52 (t, 7.8 Hz, 1H), 7.70-7.73 (d, 8.3 Hz, 1H), 7.91 (br, 1H), 8.22-8.25 (d, 7.2 Hz, 1H), 8.82 (s, 1H). LCMS (ESI pos) m/e 514 (M+1).

What is claimed is:

1. A process for preparing 4-(2-(1H-indazol-4-yl)-6-(4-(methylsulfonyl)piperazin-1-yl)methyl)thieno[3,2-d]pyrimidin-4-yl)morpholine of Formula I:

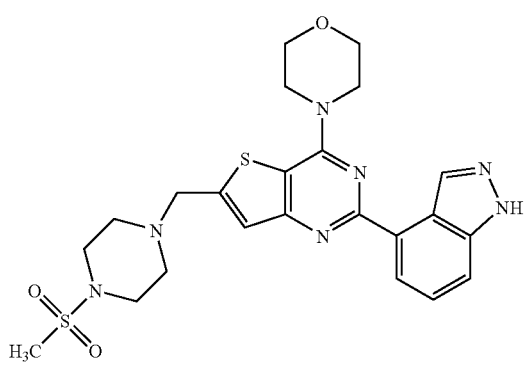

I and pharmaceutically acceptable salts thereof, comprising
(a) reacting methyl 3-aminothiophene-2-carboxylate 1 and potassium cyanate to yield thieno[3,2-d]pyrimidine-2,4 (1H,3H)-dione 2

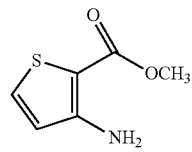

1

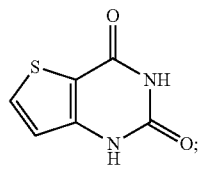

2

(b) reacting 2, phosphoryl trichloride, and N,N-dimethylaniline to yield 2,4-dichlorothieno[3,2-d]pyrimidine 3

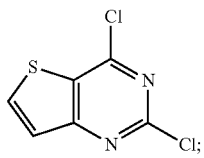

3

(c) reacting 3 and morpholine to yield 4-(2-chlorothieno[3,2-d]pyrimidin-4-yl)morpholine 4

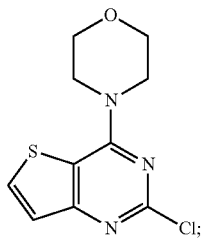

4

(d) reacting 4 with n-butyllithium and then dimethylformamide to yield 2-chloro-4-morpholinothieno[3,2-d]pyrimidine-6-carbaldehyde 5

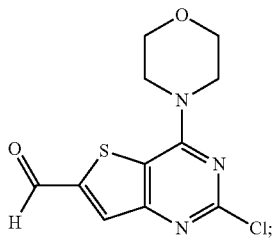

5

(e) reacting 5 and 4-(methylsulfonyl)piperazin-1-ium chloride 8 to yield 4-(2-chloro-6-((4-(methylsulfonyl)piperazin-1-yl)methyl)thieno[3,2-d]pyrimidin-4-yl)morpholine 9

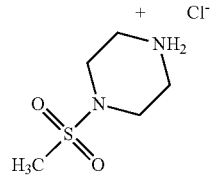

8

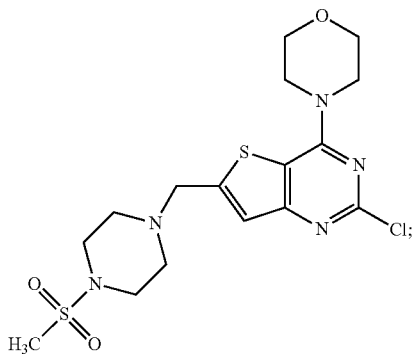

9

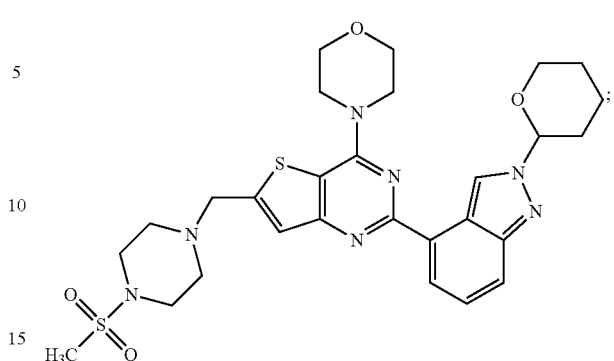

14 and (f) reacting 9, 2-(tetrahydro-2H-pyran-2-yl)-4-(4,4,5,5-tetramethyl-1,3,2-dioxaborolan-2-yl)-2H-indazole 10, and a palladium catalyst to yield 4-(6-((4-(methylsulfonyl)piperazin-1-yl)methyl)-2-(2-(tetrahydro-2H-pyran-2-yl)-2H-indazol-4-yl)thieno[3,2-d]pyrimidin-4-yl) morpholine 14

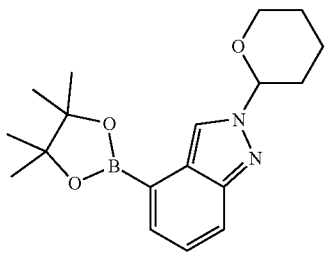

10

(g) reacting 14 with an acid to yield Formula I.

2. The process of claim 1 wherein the palladium catalyst is selected from PdCl2(PPh$_3$)$_2$, Pd(t-Bu)$_3$, PdCl$_2$ dppf CH$_2$Cl$_2$, Pd(PPh$_3$)$_4$, Pd(OAc)/PPh$_3$, Cl$_2$Pd[(Pet$_3$)]$_2$, Pd(DIPHOS)$_2$, Cl$_2$Pd(Bipy), [PdCl(Ph$_2$PCH$_2$PPh$_2$)]$_2$, Cl$_2$Pd[P(o-tol)$_3$]$_2$, Pd$_2$(dba)$_3$/P(o-tol)$_3$, Pd$_2$(dba)/P(furyl)$_3$, Cl$_2$Pd[P(furyl)$_3$]$_2$, Cl$_2$Pd(PMePh$_2$)$_2$, Cl$_2$Pd[P(4-F-Ph)$_3$]$_2$, Cl$_2$Pd[P(C$_6$F$_6$)$_3$]$_2$, Cl$_2$Pd[P(2-COOH-Ph)(Ph)$_2$]$_2$, and Cl$_2$Pd[P(4-COOH-Ph)(Ph)$_2$]$_2$.

3. The process of claim 1 further comprising treating the reaction mixture containing 14 with a palladium scavenger whereby residual palladium is removed and 14 is isolated with less than 20 ppm palladium.

4. The process of claim 3 wherein the palladium scavenger is a solid adsorbent selected from silica gel, controlled-pore glass, and derivatized low crosslinked polystyrene.

5. The process of claim 1 further comprising forming the dimesylate salt of Formula I with methanesulfonic acid in an alcohol selected from methanol, ethanol, isopropanol, butanol, and isobutanol.

* * * * *

UNITED STATES PATENT AND TRADEMARK OFFICE
CERTIFICATE OF CORRECTION

PATENT NO. : 8,354,528 B2  Page 1 of 1
APPLICATION NO. : 12/739434
DATED : January 15, 2013
INVENTOR(S) : Babu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 270 days.

Signed and Sealed this

First Day of September, 2015

Michelle K. Lee
*Director of the United States Patent and Trademark Office*